United States Patent [19]

Ishihara et al.

[11] Patent Number: 5,214,027
[45] Date of Patent: May 25, 1993

[54] PYRIDINE DERIVATIVES AND PERFUMERY COMPOSITIONS CONTAINING THE DERIVATIVES

[75] Inventors: Masakazu Ishihara, Mino; Tomoyuki Tsuneya, Ibaragi; Minoru Shiga, Toyonaka; Hiroshi Sato; Fumio Yoshida, both of Tokyo; Keiichi Yamagishi, Narashino, all of Japan

[73] Assignees: Shiono Koryo Kaisha, Ltd., Osaka; Lion Corporation, Tokyo, both of Japan

[21] Appl. No.: 863,241

[22] Filed: Apr. 3, 1992

[30] Foreign Application Priority Data

Apr. 11, 1991 [JP]  Japan ................................. 3-078799

[51] Int. Cl.[5] ................................. A61K 7/46
[52] U.S. Cl. ...................... 512/10; 546/340; 546/348; 546/350
[58] Field of Search ............... 512/10; 546/340, 348, 546/350

[56] References Cited

U.S. PATENT DOCUMENTS 3,248,363  4/1966  Farber et al. ............. 546/348
3,702,253  11/1972  Winter et al. ............. 546/340
4,374,051  2/1983  Naf et al. ................ 512/10

OTHER PUBLICATIONS

CA 116:194165q (Abstract of Eur. Pat. Appl. EP 470,391 published on Feb. 12, 1992).
Nishimoto and Nakashima, Yakugaku Zasshi, vol. 81, 82-92 (1961) (Abstract Only).
R. Kaiser, Progress in Essential Oil Research, 287-239 (1986).

*Primary Examiner*—James H. Reamer
*Attorney, Agent, or Firm*—Armstrong, Westerman, Hattori, McLeland & Naughton

[57] ABSTRACT

Described is pyridine derivatives defined according to one of generic formula (I)

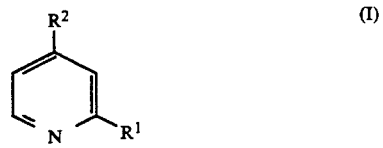

wherein $R^2$ represents isopropenyl group when $R^1$ is methyl or ethyl group, $R^2$ represents isopropenyl or acetyl group when $R^1$ is isopropenyl group, $R^2$ represents methyl group when $R^1$ is isopropyl group and $R^2$ represents isopropenyl, or isopropyl group when $R^1$ is acetyl group; and perfumery composition containing the derivatives.

2 Claims, No Drawings

PYRIDINE DERIVATIVES AND PERFUMERY COMPOSITIONS CONTAINING THE DERIVATIVES

FIELD OF THE INVENTION

This invention relates to pyridine derivatives and perfumery compositions containing the pyridine derivatives.

BACKGROUND OF THE INVENTION

Peppermint, spearmint and other essential oils are widely used as an important perfumery utilized to flavors, such as tooth powder, chewing gum and the like.

The supply and quality of natural essential oils, such as peppermint and spearmint are easily influenced by weather, and the price of the essential oils is rising. Thus, production of synthetic essential oils of spearmint, peppermint etc. are examined variously.

Almost 200 compounds have been identified as a component of spearmint essential oil (see L. Canova, 5th international Congress of Essential Oils, Abstract Paper, QT/b-22, Brazil (1971)), and preparation of synthetic spearmint essential oil using the compounds is attempted. However, a synthetic essential oil having natural feeling and taste of natural essential oil has not been obtained.

It is an object of the invention to prepare a synthetic spearmint essential oil with the same natural feeling, taste and the like as natural essential oil and to supply an inexpensive spearmint essential oil with constant quality steadily.

The inventors perceived basic compounds concretely pyridine derivatives because known components of spearmint essential oil are only neutral or acidic compounds, found that synthetic spearmint essential oils with natural feeling, taste, etc. of natural spearmint essential oil can be obtained by combinating the pyridine derivatives with known synthetic spearmint essential oil, and complete the invention.

SUMMARY OF THE INVENTION

Thus, the invention provides Pyridine derivatives defined according to one of the generic formula (I):

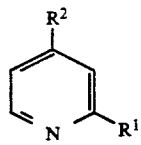

(I)

wherein $R^2$ represents isopropenyl group when $R^1$ is methyl or ethyl group, $R^2$ represents isopropenyl or acetyl group when $R^1$ is isopropenyl group, $R^2$ represents methyl group when $R^1$ is isopropyl group and $R^2$ represents isopropenyl or isopropyl when $R^1$ is acetyl group. Further the invention provides Perfumery compositions containing one or more of pyridine derivatives defined according to the generic formula (I): wherein $R^2$ represents isopropenyl group when $R^1$ is methyl or ethyl group, $R^2$ represents isopropenyl or acetyl group when $R^1$ is isopropenyl group, $R^2$ represents methyl group when $R^1$ is isopropyl group and $R^2$ represents isopropenyl or isopropyl when $R^1$ is acetyl group.

Pyridine derivatives of the invention are concretely defined as seven kinds of pyridine derivatives:
4-Isopropenyl-2-methylpyridine (hereinafter referred to as Compound I)
2-Ethyl-4-isopropenylpyridine (hereinafter referred to as Compound II)
2,4-Diisopropenylpyridine (hereinafter referred to as Compound III)
4-Acetyl-2-isopropenylpyridine (hereinafter referred to as Compound IV)
2-Isopropyl-4-methylpyridine (hereinafter referred to as Compound V)
2-Acetyl-4-isopropenylpyridine (hereinafter referred to as Compound VI)
2-Acetyl-4-isopropylpyridine (hereinafter referred to as Compound VII)

The content of these pyridine compounds I to VII used in perfumery compositions is in the range of between 1.0 ppm and 10000 ppm, preferably between 1.0 ppm and 1000 ppm.

The present compounds I to VII have individually characteristic odor in case of the high concentration, but no unplesant odor. In particular, under the highly diluted concentration, such as the content in the range between 10 ppb and 10 ppm, it was found that they are reminiscent of an interesting odor respectively somewhat changing the quality of their own odor. These pyridine compounds of the invention have the following odor discription:

Compound I : ether like, browny-acidy, raddish like ozone

Compound II : slightly nutty with a little bitter, herbal like

Compound III: earthy, slightly seaweed, somewhat

Compound IV : weak herbal green, fermented-roast feeling

Compound V : earthy green with somewhat sour and citrus

Compound VI : grassy-sweet, minty, somewhat amber like

Compound VII: grassy-green leaf, green herbal, somewhat violet

Each compound I–VII of the invention brings about the above-mentioned odor quality respectively, the plural combination of these compounds gives an excellent multiplied effect which can not be gained alone as shown in EXAMPLES 7–11.

The present compounds I to VII can be prepared by various methods, for example, by the method according to (A method) to (D method) using commercially available pyridine derivatives as a starting material.

(A method)

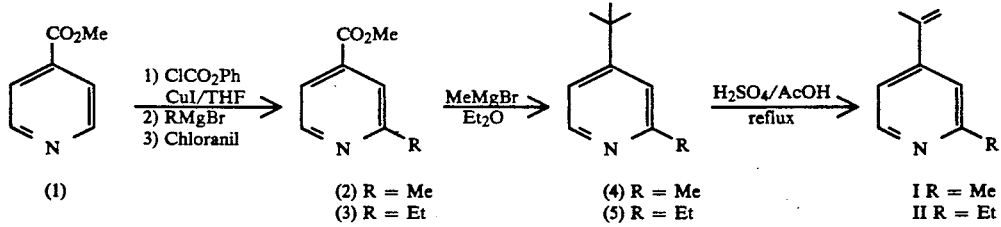

(B method)

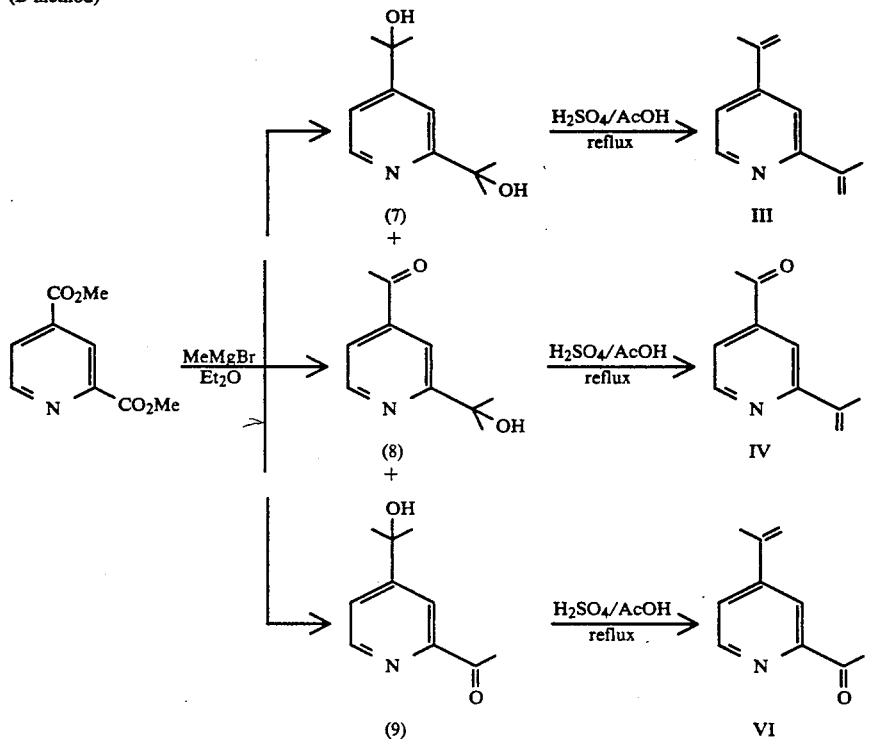

(C method)

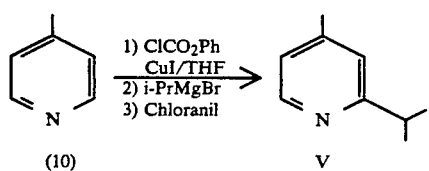

(D method)

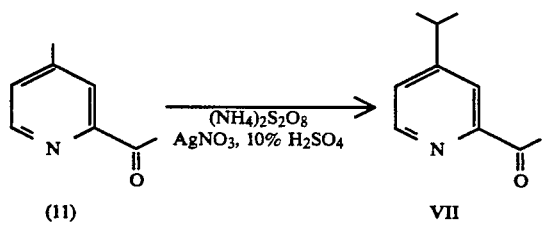

The present compounds I and II can be obtained according to the above (A method). Detailedly, 1) according to the method of D. L. Comins et al. (D. L. Comins et al., Heterocycles, 22, 151 (1984)), commercially available methyl isonicotinate (1) is converted into a pyridinium salt, 2) the salt was converted into a dihydropyridine compound by acting 1 equivalent of Grignard reagent in THF at −5° to 20° C. for 1 to 1.5 hours, and 3) the obtained dihydropyridine compound was dehydrogenated in the presence of chloranil at 65° to 75° C. for 3 to 5 hours, to give compounds (2) and (3) introduced methyl or ethyl group.

Acting 2 to 3 equivalents of methylmagnesium bromide to the compounds (2) and (3) in ether gives alcohol compounds (4) and (5), Compounds I and II being obtained by dehydration of the alcohols (4) and (5) in the presence of 6 to 20 mole of sulfuric acid in acetic acid at 100° to 120° C. for 0.5 to 1.5 hours.

The present Compounds III, IV and VI can be obtained according to (B method) Concretely, commercially available dimethyl 2,4-lutidinate (6) is used as a starting material, the diol compound (7), hydroxyketone compounds (8) and (9) were obtained after separation and purification by acting 3 to 6 equivalents of methylmagnesium bromide to the ester (6) in ether, followed by dehydrating the compounds (7), (8) and (9) in the sulfuric acid/acetic acid system in the same manner as the above (A method).

As shown in (C method), the present Compound V can be synthesized in the same manner as (A method) except that γ-picoline (10) was used in place of methyl isonicotinate, and isopropylmagnesium bromide was used as a Grignard reagent.

The present Compound VII was produced according to the above (D method). Appling the method of F. Minisci et al. (F. Minisci, et al., Tetrahedron, 27, 3575 (1971)) to the preparation of Compound VII, the Compound VII was obtained by selective attacking the decarbonated radical of isobutyric acid at the 4-position of 2-acetylpyridine.

The objected compound in each process, thus obtained, can be easily purified by conventional separation method, such as solvent extraction, distillation method, recrystalization method, column chromatography, preparative thin-layer chromatography etc.

As a component mixed with a pyridine derivative in the present perfumery compositions, exemplified are carboxylic acids, such as acetic acid, diethylacetic acid, propionic acid, cinnamic acid and the like, phenols, such as 2,6-dimethylphenol, eugenol and the like, esters, such as ethyl acetate, ethyl butyrate, geranyl acetate, cinnamyl acetate, 3-octyl acetate, menthyl acetate, carvyl acetate, cis-3-hexenyl 2-methylbutyrate, isoamyl isovalerate, β-phenetyl 2-methylbutyrate, isoamyl 2-methylbutyrate, alkylcyclohexane propionate and the like, aldehydes, such as benzaldehyde, vanillin, undecanal, dodecanal and the like, alcohols, such as carveol, dihydrocarveol, α-terpineol, terpinene-4-ol, 3-octanol, 3-nonanol, 3-decanol, linalool, cis-3-hexenol, 1-octene-3-ol and the like, and other compounds, such as 1,8-cineol, 2-acetylpyridine, 2-acetylpyrrole, menthone, menthofuran, carvone, dihydrocarvone, caryophyllene, cis-jasmone, spearmint terpene, peppermint terpene, grapefruit oil, geranium oil.

Using the pyridine derivatives of the invention makes it possible to produce synthetic spearmint essential oil having the same natural feeling, taste and the like as a natural essential oil and to provide an inexpensive spearmint essential oil of constant quality steadily. Further, the perfumery composition containing the pyridine derivatives can be utilized in a wide variety of fields, such as food, cosmetics and the like due to characteristic oder based on each derivative.

EXAMPLE 1

Preparation of 4-isopropenyl-2-methylpyridine (Compound I)

First Steps: Preparation of Methyl 2-methylisonicotinate (2)

Under argon gas atmosphere, methyl isonicotinate (21 g, 0.15mol), copper (I) iodide (1.4 g, 7.35 mmol), dimethylsulfide (20 ml) and THF (200 ml) were added to a reaction container, the mixture was cooled at −20° C. with an ice-methanol bath, then an ethyl chloroformate (23.5 g, 0.15 mol) in THF (20 ml) solution was added dropwise to the mixture at about 15° C. (inner temperature) with stirring.

After dropwise addition, the mixture was stirred at the same temperature for 15 minutes, and ether solution of 3M methylmagnesium bromide (60 ml) was slowly added dropwise at over 5° C. After dropwise addition, the temperature of the mixture was slowly elevated to room temperature, and then the mixture was further stirred for 1 hour.

The reaction mixture was poured into a cooled 20% ammonium chloride solution (350 ml), and the mixture was extracted with a mixed solvent of ether/hexane (1 : 1). The organic layer was washed once with brine twice with dilute hydrochloric acid and once again with brine. The washed organic layer was dried over anhydrous magnesium sulfate, the solvent being evaporated under reduced pressure, the residue being roughly purified with silica gel column chromatography to give 27 g of a yellow oil of dihydropyridine compound. The oil (27 g) and chloranil in the solvent mixture of acetic acid (80 ml) and toluene (150 ml) were stirred at about 70° C. for 4 hours. To the mixture, toluene (150 ml) and ethyl acetate (150 ml) was added, and the mixture was washed with 20% sodium hydroxide solution and 10% sodium hydroxide solution, and the organic layer was extracted three times with diluted hydrochloric acid. The diluted hydrochloric acid extracts were combined, neutralized with 20% sodium hydroxide and then extracted three times with ether. The ether extracts were combined, washed once with brine, and then dried over anyhydrous magnesium sulfate. The solvent was evaporated under reduced pressure. The residue was purified through silica gel column chromatography to give 9.6 g of compound (2) as a yellow oil (yield: 42.4%)

Second Steps: Preparation of 2-methy4-(2-hydroxypropan-2-yl)pyridine (4)

While stirring and cooling (inner temperature: 5° to 12° C.), 3M methylmagnesium bromide was added dropwise to ether (100 ml) solution of compound (2) (9.6 g, 64 mmol). After dropwise addition, the mixture was stirred at room temperature for 1 hour and further stirred under reflux for 1 hour.

The reaction mixture was poured into a cooled saturated ammonium chloride solution, and the mixture was extracted three times with a mixed solvent of ethyl acetate/ether (2 : 1). The organic layer was washed once with brine and dried over anhydrous magnesium sulfate. The solvent was evaporated under reduced pressure to give 8.3 g of a brown oil. The oil (8.3 g) was purified through silica gel column chromatography (solvent: ether/hexane=1 : 1) to give 6.1 g of the alcohol compound (4) as a pale-yellow oil (yield: 63.5%).

Third Steps: Preparation of 2-methyl-4-isopropenylpyridine (Compound I)

The mixture of the alcohol compound (4) (6.1 g, 40 mmol), conc. sulfuric acid (15 g) and acetic acid (35 g) were refluxed with stirring for 1 hour.

The reaction mixture was poured into an ice water (100 ml), and the mixture was extracted once with toluene. The aqueous layer was basified with a 20% sodium hydroxide solution, and the basic solution was extracted three times with a mixed solvent of ethyl acetate/ether (1 : 1). The combined organic extracts were washed once with brine and dried over anhydrous magnesium sulfate. The solvent was evaporated under reduced pressure. The residue was purified through silica gel column chromatography (solvent: ether/hexane =1 : 5) to give 3.14 g of Compound I as a colorless oil (yield: 59%)

(Spectral Date of Compound I)

IR(film) $\nu$ (cm$^{-1}$) 1600, 1543, 900, 835;

$^1$H—NMR(CDCl$_3$) $\delta$ 2.14(m, 3H, CH$_3$), 2.56(s, 3H, CH$_3$), 5.21(m, 1H, CH$_2$=), 5.51(m, 1H, CH$_2$=), 7.12(d, J=5 Hz, 1H, ArH), 7.16(s, 1H, ArH), 8.43(d, J=5 Hz, 1H, ArH); EI—MS, m/z(rel. int.) 133(M$^+$, 100), 132(30), 118(19), 117(18), 91(33), 65(11); HR—MS calcd for C$_9$H$_{11}$N$_1$ [M+] $^{m/z}$ 133.0891, found [M+] $^{m/z}$ 133.0991.

EXAMPLE 2

Preparation of 2-Ethyl-4-isopropenylpyridine (Compound II)

The synthesis of Compound II was performed in the same manner as First steps of example 1 except that ethyl magnesium bromide was used in place of methylmagnesium bromide. Compound II was obtained as a colorless oil (total yield: 12%).

IR(film) $\nu$ (cm$^{-1}$) 1600, 1543, 900, 840. $^1$H—NMR(60MHz, CDCl$_3$) $\delta$ 1.31(t, J=7 Hz, 3H, CH$_3$), 2.11(m, 3H, CH$_3$), 2.83(q, J=7 Hz, 2H, CH$_2$), 5.18(m, 1H, CH$_2$=), 5.49(m, 1H, CH$_2$=), 7.08(d, J=5 Hz, 1H, ArH), 7.12(s, 1H, ArH), 8.43(d, J=5 Hz, 1H, ArH); EI—MS, m/z(rel. int.) 147(M$^+$, 70), 146(100), 130(5), 119(21), 91(7), HR—MS calcd for C$_{10}$H$_{13}$N$_1$ [M+]m/z 147.1047, found [M+]m/z 147.1032.

EXAMPLE 3

Preparation of 2,4-Diisopropenylpyridine (Compound III)

First Steps: Preparation of 2,4-bis(2-hydroxypropan-2-yl)pyridine (7), 2-(2-hydroxypropan-2-yl)-4-acetylpyridine (8) and 2-acetyl-4-(2-hydroxypropan-2-yl)pyridine (9)

To a solution of dimethyl 2,4-lutidinate(39 g, 0.2 mol) in ether(400 ml) was added dropwise 3M methylmagnesium bromide in ether (400 ml, 1.2 mol), with stirring and cooling with an ice water bath (internal temperature of the reaction mixture: 5° to 12° C.). After being stirred for 1 h at room temperature, the reaction mixture was refluxed for an additional 1 h. The reaction mixture was poured into a cold saturated NH$_4$Cl solution. The aqueous layer was extracted three times with a mixed solvent (ether/ethyl acetate=1:2). The combined organic layer was washed with brine and dried (MgSO$_4$). After removal of the solvent, the brownish oil (39.2 g) was chromatographed over silica gel (ether/hexane=8:2) to give 22.7 g (yield: 58%) of the compound (7) as colorless crystals and 11.7 g (yield: 33%) of a 1:1 mixture of the compounds (8) and (9) as a colorless oil.

{Spectral data of compound (7)}

IR (KBr) $\nu$ (cm$^{-1}$):3280, 2960, 1600, 1180, 1102, 955. $^1$H—NMR(60MHz, CDCl$_3$, $\delta$ ppm): 1.48(s, 6H), 1.51(s, 6H), 3.60(br.s, 1H), 5.12 (br. S, 1H), 7.139 (dd, J=1.6 and 5.0 Hz, 1H), 7.42 (d, J=1.6 Hz, 1H), 8.25(d, J=5.0 Hz, 1H). EI—MS, m/z(rel. int.) 194(M$^+$—1,8), 180(100), 165(12), 138(20), 137(22).

{Spectral data of compound (8)}

EI—MS, m/z, (rel. int.): 179(M$^+$, 100), 164(58), 137(72), 78(35), 59(43), 43(63).

{Spectral data of compound (9)}

EI—MS, m/z (rel. int.): 179(M$^+$, 5), 164(100), 121(33), 59(13), 43(5).

The diol (7)(20g, 0.1 mol) was refluxed with stirring in conc. H$_2$SO$_4$(50g) and acetic acid(118g) for 1 hour. The reaction mixture was cooled and poured into an ice water (350 ml) and washed with toluene. The aqueous layer was basified with 20% NaOH and extracted three times with a mixed solvent(ether/ethyl acetate=1:1). The organic layer was washed with brine and dried(MgSO$_4$). After removal of the solvent, the residue was chromatographed over silica gel(ether/hexane=1:5) to give 12.5 g(78%) of the compound III as a colorless oil.

Spectral Data of Compound III

IR(film) $\nu$ (cm$^{-1}$):3100, 1598, 900, 843. $^1$H—NMR(60MHz, CDCl$_3$) $\delta$2.07(m, 3H), 2.17(m, 3H), 5.16(m, 2H), 5.45(m, 1H), 5.74 (m, 1H), 7.04(dd, J=1.6 and 5 Hz, 1H), 7.35(d, J=1.6Hz, 1H), 8.36(d, J=5Hz, 1H). EI—MS, m/z(rel. int.):159(M$^+$, 100), 158(86), 144(18), 119(25), 91(13).

EXAMPLE 4

Preparation of 4-acetyl-2-isopropenylpyridine (Compound IV) and 2-acetyl-4-isopropenylpyridine (Compound VI)

The mixture of compounds (8) and (9) (1:1) (4g, 20 mmol) obtained in example 3, H$_2$SO$_4$(13g) and acetic acid(30g) were refluxed with stirring for 1.5 hours. The reaction mixture was poured into an ice water(50 ml) and was extracted with a mixed solvent of ether and toluene (1:1). The aqueous layer was basified with 20% aq. NaOH and was extracted three times with ether. The combined ether layer was washed with brine and dried(MgSO$_4$). After removal of the solvent, the residue was chromatographed over silica gel (ether/hexane=15:85) to give 1.33 g of compound IV as a colorless oil(yield:37%) and 1.22 g of compound VI as a colorless oil(yield:34%).

Spectral Data of Compound IV

IR (film) $\nu$ (cm$^{-1}$):3100, 1700, 1590, 1365, 1250, 910, 850.

$^1$H—NMR(60MHz, CDCl$_3$) $\delta$ 2.24(m, 3H), 2.60(s, 3H), 5.36(m, 1H), 5.94(m, 1H), 7.56(dd, J=1.6 and 5Hz, 1H), 7.88(d, J=1.6Hz, 1H), 8.74(d, J=5Hz, 1H).

EI—MS, m/z(rel.int.):161(M$^+$, 100), 160(70), 146(12), 118(30), 117(20), 91(18), 43(25).

Spectral Data of Compound VI

IR (film) $\nu$ (cm$^{-1}$):3100, 3070, 1700, 1598, 1250, 910, 853.

$^1$H—NMR(60MHz, CDCl$_3$) $\delta$ 2.17(br.s, 3H), 2.65(s, 3H), 5.28(m, 1H), 5.61 (m, 1H), 7.43(dd, J=1.6 and 5Hz, 1H), 7.97(d, J=1.6Hz, 1H), 8.54(d, J=5Hz, 1H).

EI—MS, m/z (rel. int.):161(M$^+$, 86), 133(28), 119(100), 118(65), 91(31), 43(30).

EXAMPLE 5

Preparation of 2-isopropyl-4-methylpyridine (Compound V)

To a stirred solution of 4-picoline(10g, 0.11 mol) and CuI(0.8g, 4 mmol) in 230 ml of THF was added dropwise phenyl chloroformate(17g, 0.11 mol) at −15° C. (inner temperature) under Ar. After 5 min, isopropyl magnesium bromide(0.17 mol) in 60 ml of ether was added dropwise over 15 min. The mixture was stirred for 30 min at below −5° C. and then at room temperature for another 1 hour followed by being poured into an aqueous 20% NH$_4$Cl solution(120 ml). Ether(50 ml) was added and the organic layer was washed with aqueous 5% NaOH solution, water and brine. After drying (MgSO$_4$), the solution was concentrated to yield 25.5 g of a reddish oil. The crude oil was treated with chloranil(32g, 0.13 mol) in acetic acid(35 ml) and toluene(100 ml) at 70° C. for 4.5 h. The reaction mixture was cooled and extracted twice with 10% HCl. The acid extracts were washed with toluene and made basic with aqueous 15% NaOH solution and extracted with ether. The ether extracts were washed twice with brine and dried(MgSO$_4$) After removal of the solvent, the residue was chromatographed over silica gel(hexane/ether=4:1) to give 6.53 g(44%) of Compound V as a colorless oil:

IR(film) $\nu$ (cm$^{-1}$):3080, 1603, 1562, 820;

$^1$H—NMR(60MHz, CCl$_4$) $\delta$ 1.25(d, J=7Hz, 6H, CH3), 2.25(s, 3H, CH3), 2.94(dq, J=7 and 7Hz, 1H, CH), 6.76(d, J=5Hz, 1H, ArH), 6.81(s, 1H, ArH), 8.26(d, J=5Hz, 1H, ArH); EI—MS, m/z (rel.int.) 135(M$^+$, 40), 134(42), 120(100), 107(28), 93(23), 77(3), 65(5); HR—MS calcd. for C$_9$H$_{13}$N$_1$ [M$^+$] m/z 135.1047, found [M$^+$] m/z 135.1068.

EXAMPLE 6

Preparation of 2-acetyl-4-isopropylpyridine (Compound VII)

To a solution of 2-acetylpyridine (11) (14.4 g, 0.12 mol), isobutyric acid (32 g, 0.36 mol) and AgNO$_3$(4 g, 24 mmol) in 10% H$_2$SO$_4$(70 ml) which were heated at 70° C., was added dropwise a solution of NH$_4$S$_2$O$_8$(52 g, 0.23 mmol) in H$_2$O(120 ml) for 15 min between 70–80° C. After evolution of CO$_2$ ceased, the reaction mixture was stirred at about 80° C. for 15 min and cooled. The solution was washed with ether and the aqueous layer was adjusted at pH 8.0 with sat. K$_2$CO$_3$ solution and extracted three times with ether/ethyl acetate (1 : 1). The organic layer was washed with brine and dried(MgSO$_4$) After removal of the solvent, the residue was chromatographed over silica gel (ether/hexane=3:7) to yield 5.96 g(30.7%) of the comound VII as a colorless oil:

IR(film) $\nu$ cm$^{-1}$: 3080, 1700, 1599, 1358, 1202, 843;

$^1$H—NMR(60MHz, CDCl$_3$) $\delta$ 1.25(d, J=7Hz, 6H, two CH3), 2.67(s, 3H, CH3), 2.96(dq, J=7 and 7Hz, 1H, CH), 7.27(dd, J=1.5 and 5Hz, 1H, ArH), 7.87(d, J=1.5Hz, 1H, ArH), 8.50(d, J=5Hz, 1H, ArH);

EI—MS m/z(rel.int.); HR—MS calcd. for C$_{10}$H$_{13}$N$_1$O$_1$ [M$^+$] m/z 163.0996, found [M$^+$] m/z 163.1015.

EXAMPLE 7

Spearmint flavor compositions were prepared by formulating ingredients (parts by weight) shown in Table 1 below.

TABLE 1

| Ingredients | Formula A | Formula B |
|---|---|---|
| 3-Octanol | 15.0 | 15.0 |
| Menthone | 9.0 | 9.0 |
| Dihydrocarvone | 10.0 | 10.0 |
| β-Caryophyllene | 5.0 | 5.0 |
| Carveol | 4.0 | 4.0 |
| Carvyl acetate | 1.8 | 1.8 |
| Dihydrocarveol | 2.0 | 2.0 |
| α-Terpineol | 1.6 | 1.6 |
| 3-Octyl acetate | 1.5 | 1.5 |
| Terpinen-4-ol | 1.7 | 1.7 |
| cis-3-Hexenyl isovalerate | 1.5 | 1.5 |
| cis-3-Hexenyl 2-methylbutyrate | 1.0 | 1.0 |
| 3-Nonanol | 0.5 | 0.5 |
| 3-Decanol | 0.4 | 0.4 |
| Linalool | 0.5 | 0.5 |
| cis-Jasmone | 0.8 | 0.8 |
| β-Phenylethyl alcohol | 0.6 | 0.6 |
| Eugenol | 0.2 | 0.2 |
| Spearmint Terpene | 120.0 | 120.0 |
| Compound II | 0.0005 | 0.0 |
| Compound III | 0.001 | 0.0 |
| Compound VI | 0.002 | 0.0 |
| 1-Carvone | 822.8965 | 822.9 |
| Total | 1000.0 | 1000.0 |

The sensory evaluation regarding Formulas A and B by 11 members of flavor panelists resulted in that 10 out of 11 members pointed out that A formula containing the mixtures of compound II, III and VI gave an excellent naturality having sweet hay odor with a bit fishy peculiar to spearmint flavor compared to B formula substituted by 1-Carvone instead of compound II, III and VI.

EXAMPLE 8

Peppermint flavor composition were prepared by formulating ingredients shown in Table 2 below.

TABLE 2

| Ingredients | Formula A | Formula B |
|---|---|---|
| Menthone | 250.0 | 250.0 |
| Menthofuran | 2.5 | 2.5 |
| 1,8-Cineol | 10.0 | 10.0 |
| 1-Octen-3-ol | 2.0 | 2.0 |
| Pulegone | 14.0 | 14.0 |
| Menthyl acetate | 55.0 | 55.0 |
| Caryophyllene | 20.0 | 20.0 |
| α-Terpineol | 5.0 | 5.0 |
| Terpinen-4-ol | 3.0 | 3.0 |
| Linalool | 1.0 | 1.0 |
| Isopentyl isovalerate | 1.5 | 1.5 |
| Isopentyl 2-methylbutyrate | 1.0 | 1.0 |
| cis-Jasmone | 0.8 | 0.8 |
| Eugenol | 0.3 | 0.3 |
| β-Phenylethyl isovalerate | 0.5 | 0.5 |
| Compound I | 0.0005 | 0.0 |
| Compound II | 0.001 | 0.0 |
| Compound III | 0.002 | 0.0 |
| Peppermint terpene | 140.0 | 140.0 |
| 1-Menthol | 493.3965 | 493.4 |
| Total | 1000.0000 | 1000.0 |

The sensory evaluation regarding formulas A and B by 11 members of flavor panelists resulted in that 9 out of 11 members pointed out that A formula containing the mixtures of compound I, II and III gave an excellent naturality having herbal green odor with fresh sweetness peculiar to peppermint Mitcham type compared to B formula substituted by 1-Menthol instead of compound I, II and III.

EXAMPLE 9

Guava flavor compositions were prepared by formulating ingredients shown in Table 3 below.

TABLE 3

| Ingredients | Formula A | Formula B |
| --- | --- | --- |
| Diethyl acetic acid | 10.0 | 10.0 |
| Acetic acid | 10.0 | 10.0 |
| Propionic acid | 10.0 | 10.0 |
| Benzaldehyde | 1.0 | 1.0 |
| Cinnamyl acetate | 0.3 | 0.3 |
| Ethyl acetate | 2.0 | 2.0 |
| cis-3-Hexenol | 5.0 | 5.0 |
| α-Terpineol | 2.0 | 2.0 |
| Cinnamic acid | 1.0 | 1.0 |
| Ethyl butyrate | 2.0 | 2.0 |
| cis-3-Hexenyl acetate | 0.5 | 0.5 |
| Allylcyclohexane propionate | 1.0 | 1.0 |
| Grapefruit oil | 100.0 | 100.0 |
| Compound III | 0.01 | 0.0 |
| Compound V | 0.01 | 0.0 |
| Compound VII | 0.03 | 0.0 |
| Triacetin | 855.15 | 855.2 |
| Total | 1000.00 | 1000.0 |

The sensory evaluation regarding formulas A and B by 11 members of flavor panelists resulted in that 8 out of 11 member pointed out that A formula containing the mixtures of compound III, V and VII gave an excellent naturality having sweet tropical odor peculiar to guava flesh compared to B formula substituted by Triacetin instead of compounds III, V and VII.

EXAMPLE 10

Shrimp flavor compositions were prepared by formulating ingredients shown in Table 4 below.

TABLE 4

The following mixtures of A and B Formula are prepared (parts by weight):

| Ingredients | Formula A | Formula B |
| --- | --- | --- |
| 2-Acetylpyridine | 56.0 | 56.0 |
| 2-Acetylpyrrole | 20.0 | 20.0 |
| 2,6-Dimethylphenol | 15.0 | 15.0 |
| Ethyl octanoate | 9.0 | 9.0 |
| 2,4-Decadienol | 3.0 | 3.0 |
| Pyridine | 0.8 | 0.8 |
| 2-Octenal | 1.0 | 1.0 |
| 2-Nonenal | 0.8 | 0.8 |
| Octanoic acid | 0.8 | 0.8 |
| 2-Decenal | 1.6 | 1.6 |
| 2-Dodecenal | 0.6 | 0.6 |
| Ethyl laurate | 1.8 | 1.8 |
| Ethyl myristate | 0.8 | 0.8 |
| Diacetin | 32.0 | 32.0 |
| Methylthiomethylpyrazine | 0.02 | 0.02 |
| Compound II | 0.3 | 0.0 |
| Compound IV | 0.1 | 0.0 |
| Vegetable oil | 856.38 | 856.78 |
| Total | 1000.00 | 1000.00 |

The sensory evaluation regarding formulas A and B by 11 members of flavor panelists resulted in that 8 out of 11 members pointed out that A formula containing the mixtures of compound II and IV gave an excellent naturality having the shell flavor peculiar to shrimp flesh compared to B formula substituted by vegetable oil instead of compounds II and IV.

EXAMPLE 11

Rose fragrance compositions were prepared by formulating ingredients shown in Table 5 below.

TABLE 5

| Ingredients | Formula A | Formula B |
| --- | --- | --- |
| β-Phenylethyl alcohol | 90.0 | 90.0 |
| Geraniol | 400.0 | 400.0 |
| Rose oil burgalia | 100.0 | 100.0 |
| α-Ionone | 40.0 | 40.0 |
| Linalool | 15.0 | 15.0 |
| Geranyl acetate | 35.0 | 35.0 |
| Geranium oil | 60.0 | 60.0 |
| Eugenol | 10.0 | 10.0 |
| Nerol | 200.0 | 200.0 |
| Undecanal | 2.0 | 2.0 |
| Dodecanal | 2.0 | 2.0 |
| Vanillin | 5.0 | 5.0 |
| Compound I | 1.3 | 0.0 |
| Compound VI | 0.7 | 0.0 |
| Triethyl citrate | 39.0 | 41.0 |
| Total | 1000.0 | 1000.0 |

The sensory evaluation regarding formulas A and B by 11 members of flavor panelists resulted in that 8 out of 11 members pointed out that A formula containing the mixture of compounds I and VI improved synthetic and hard odor into soft and sweet odor with an excellent naturality reminiscent of top note of rose compared to B formula substituted by Triethyl citrate instead of compound I and VI.

What is claimed is:

1. Pyridine derivatives of the generic formula (I):

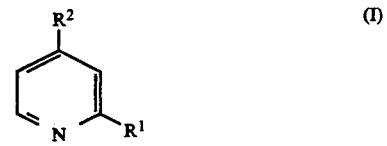

wherein $R^2$ represents an isopropenyl when $R^1$ is a methyl or an ethyl group, $R^2$ represents an isopropnyl or an acetyl group when $R^1$ is an isopropenyl group, $R^2$ represents a methyl group when $R^1$ is an isopropyl group and $R^2$ represents an isopropenyl or an isopropyl group when $R^1$ is an acetyl group.

2. Perfumery compositions containing one or more of pyridine derivatives of the generic formula (I):

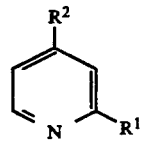

wherein $R^2$ represents an isopropenyl group when $R^1$ is a methyl or an ethyl group, $R^2$ represents an isopropenyl or an acetyl group when $R^1$ is an isopropenyl group, $R^2$ represents a methyl group when $R^1$ is an isopropyl group and $R^2$ represents an isopropenyl or an isopropyl group when $R^1$ is an acetyl group.

* * * * *